(12) United States Patent
Jackson

(10) Patent No.: US 6,738,651 B1
(45) Date of Patent: May 18, 2004

(54) CATHETER BASED PROBE AND METHOD OF USING SAME FOR DETECTING CHEMICAL ANALYTES

(75) Inventor: Gregg A. Jackson, Mountain View, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 10/194,111

(22) Filed: Jul. 11, 2002

Related U.S. Application Data

(63) Continuation of application No. 09/522,309, filed on Mar. 9, 2000, now Pat. No. 6,498,941.

(51) Int. Cl.[7] .............................................. A61B 5/00
(52) U.S. Cl. ...................... 600/310; 600/325; 600/327; 600/435; 600/585
(58) Field of Search ................................ 600/309–312, 600/317, 337, 322–27, 329, 332, 339, 508–510, 585, 433–435

(56) References Cited

U.S. PATENT DOCUMENTS

| | | | | |
|---|---|---|---|---|
| 4,403,984 A | * | 9/1983 | Ash et al. ................... 604/503 |
| 4,768,858 A | * | 9/1988 | Hussein ................... 350/96.32 |
| 4,816,419 A | | 3/1989 | Halfman |
| 4,849,172 A | * | 7/1989 | Yafuso et al. ................. 422/55 |
| 4,850,358 A | * | 7/1989 | Millar ........................ 600/486 |
| 4,937,457 A | * | 6/1990 | Mitchell ................... 250/458.1 |
| 5,166,990 A | * | 11/1992 | Riccitelli et al. .............. 385/12 |
| 5,196,709 A | | 3/1993 | Berndt et al. |
| 5,222,949 A | * | 6/1993 | Kaldany ..................... 604/524 |
| 5,239,057 A | | 8/1993 | Wang et al. |
| 5,330,718 A | * | 7/1994 | Hui et al. ................ 422/82.07 |
| 5,456,680 A | * | 10/1995 | Taylor et al. .................. 606/2 |
| 5,498,549 A | * | 3/1996 | Nagel et al. ................. 436/172 |
| 5,615,673 A | * | 4/1997 | Berger et al. ................ 600/326 |
| 5,624,847 A | * | 4/1997 | Lakowicz et al. ............. 436/68 |
| 5,660,991 A | | 8/1997 | Lakowicz et al. |
| 5,833,603 A | * | 11/1998 | Kovacs et al. .............. 600/317 |
| 5,912,179 A | * | 6/1999 | Alvarez et al. ............. 600/310 |
| 6,498,941 B1 | * | 12/2002 | Jackson ..................... 600/310 |

OTHER PUBLICATIONS

"Emerging Biomedical and Advanced Applications of Time–Resolved Fluorescence Spectroscopy," Journal of Fluorescence, vol.4, No1, 1994.

* cited by examiner

*Primary Examiner*—Max F. Hindenburg
*Assistant Examiner*—Matthew J Kremer
(74) *Attorney, Agent, or Firm*—Blakely, Sokoloff, Taylor & Zafman LLP

(57) ABSTRACT

A medical diagnostic apparatus including a catheter and a probe assembly coupled to the catheter and a method involving the use of a catheter and a probe assembly coupled to the catheter. The probe assembly is capable of detecting a chemical analyte. The probe assembly includes a detection probe located within the catheter. The detection probe can be fixedly attached to the catheter or slideable within the catheter.

5 Claims, 6 Drawing Sheets

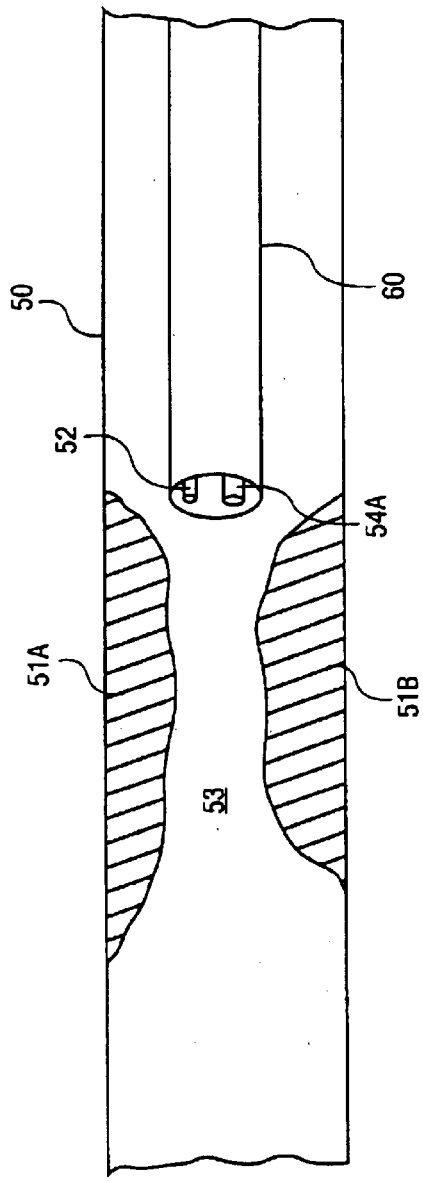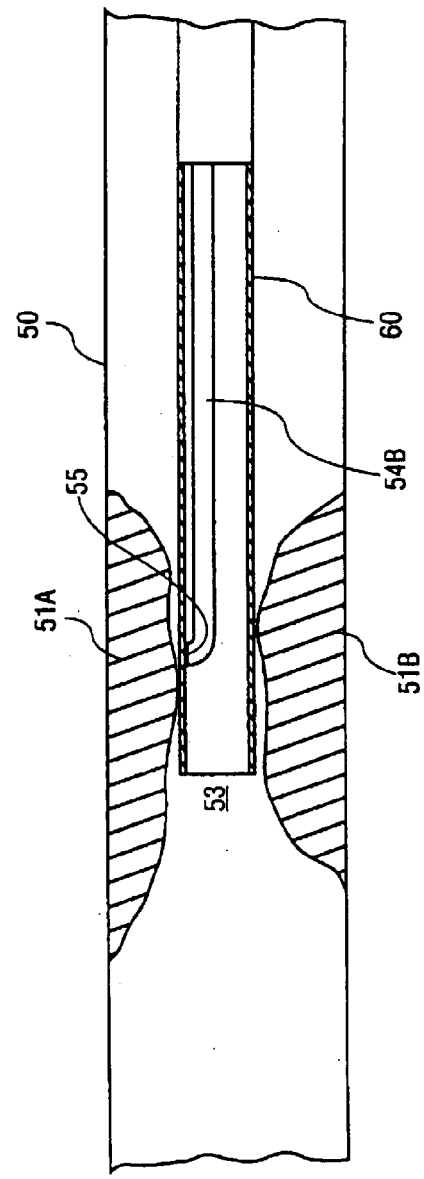

CATHETER BASED PROBE AND METHOD OF USING SAME FOR DETECTING CHEMICAL ANALYTES

RELATED APPLICATIONS

This is a continuation of application Ser. No. 09/522,309, filed on Mar. 9, 2000, now U.S. Pat. No. 6,498,941.

BACKGROUND OF THE INVENTION

1. Field of the Invention

The present invention relates generally to medical diagnostic devices, and more specifically to catheter based probes.

2. Background Information

An accurate diagnosis of a vascular disease allows a doctor to choose an appropriate therapeutic treatment. A vessel can be afflicted with different vascular diseases ranging from less severe conditions, such as thrombosis, to extremely severe conditions, such as chronic total occlusion.

Various diagnostic procedures such as an angiogram and intravascular ultrasound (IVUS) help provide some information regarding the vascular diseases being confronted by the doctor. However, many existing diagnostic devices and procedures do not provide enough information and are not consistently accurate. For example, an angiogram produces a silhouette that indicates the degree of constriction in a vessel, but the silhouette does not indicate what is causing the constriction and does not provide any chemical information about the diseased area. Furthermore, IVUS produces an image which can be difficult to interpret and is subject to poor signal transmission. IVUS also fails to provide any chemical information about the diseased area.

Because different vascular conditions are associated with different chemicals, the ability to detect the presence of particular chemicals in the vasculature would provide doctors with more accurate information regarding the vascular diseases afflicting a patient. With such information, a doctor could treat a patient's vascular diseases using more appropriately tailored treatments.

SUMMARY OF THE INVENTION

The present invention provides a medical diagnostic apparatus having a catheter and a probe assembly coupled to the catheter. The probe assembly is capable of detecting a chemical analyte. In one embodiment of the present invention, the probe assembly includes a detection probe disposed within the catheter. In another embodiment, the detection probe includes an elongated member having a distal end formed with an optically clear cover and a membrane embedded with an analyte indicator.

The present invention also provides a method for detecting a chemical analyte. In one embodiment of the present invention, the method includes inserting a catheter in a lumen, advancing the catheter through the lumen, inserting a first detection probe within the catheter, and advancing the first detection probe through the catheter to a first target area.

Additional features and benefits of the present invention will become apparent from the detailed description, figures and claims set forth below.

BRIEF DESCRIPTION OF THE DRAWINGS

Various embodiments of the present invention will be described in detail with reference to the following drawings in which like reference numerals refer to like elements. The present invention is illustrated by way of example and not limitation in the accompanying figures.

FIG. 4A shows one embodiment of a catheter fitted with a detection probe, both of which are positioned adjacent to a diseased area of a vessel in accordance with the teachings of the present invention.

FIG. 4B shows another embodiment of a catheter fitted with a detection probe, both of which are positioned adjacent to a diseased area of a vessel in accordance with the teachings of the present invention.

DETAILED DESCRIPTION

Figure 1:
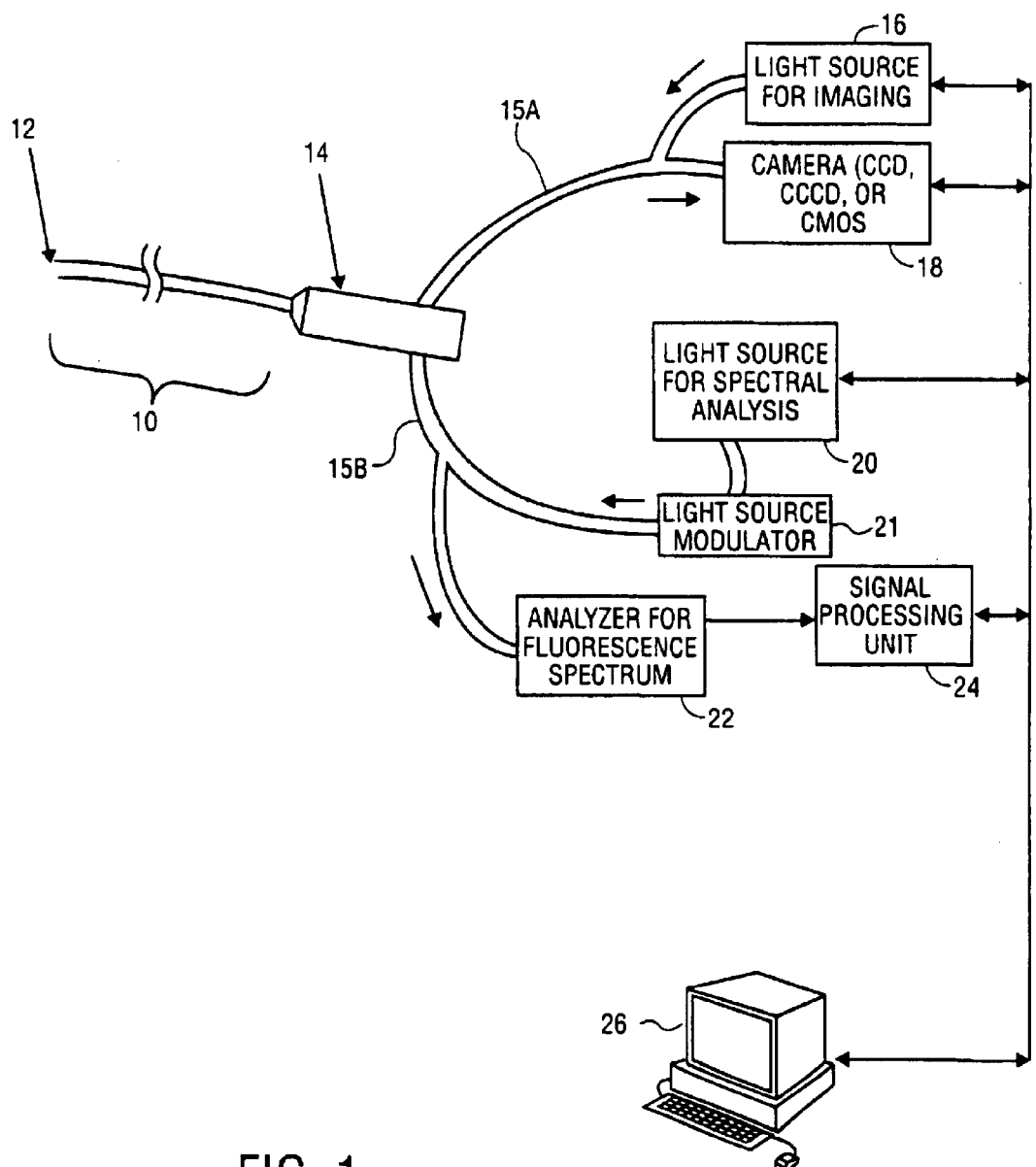
FIG. 1 shows a catheter based probe system in accordance with the teachings of the present invention.

The following description provides embodiments of the present invention. However, it will be appreciated that other embodiments of the present invention will become apparent to those of ordinary skill in the art upon examination of this description. Thus, the present description and accompanying drawings are for purposes of illustration and are not to be used to construe the invention in a restrictive manner.

A procedure called Lifetime-Based Sensing Fluorescence Spectroscopy (LBSFS) provides chemical information by measuring the change in a probe's lifetime fluorescence when in the presence of certain chemical analytes. The probe is embedded with a fluorophore which experiences a known change in lifetime fluorescence in the presence of a particular chemical analyte. For example, the fluorophores calcium green (CaG), calcium orange (CaO), calcium crimson (CaC), Quin-2, Fura-2 and Indo-1 have been shown to exhibit a distinct lifetime signature in response to calcium (Ca). Furthermore, the fluorophores coronene, benzo[g, h, I]perylene and 2,5 dansyl have been shown to exhibit a distinct lifetime signature in response to oxygen ($O_2$). Thus, different fluorophores can be used to detect the presence of different chemical analytes. Images are created through the processing of the phase shift and modulation signals received from the probe. The phase and modulation values are typically obtained through an image intensifier and charged coupled device (CCD), three charged coupled device (CCCD) or complementary metal oxide semiconductor (CMOS) based camera system.

More detailed background information regarding fluorescence spectroscopy is discussed in an article titled "Emerging Biomedical and Advanced Applications of Time-Resolved Fluorescence Spectroscopy" by Lakowicz et al. in the *Journal of Fluorescence,* vol. 4, no. 1 (1994). For example, according to Lakowicz et al., probes such as the CaG series and $Mg^{2+}$ all display changes in lifetime in response to binding their specific cations. When a change in lifetime occurs, the probe displays detectable emission from both the free and the cation-bound forms. The lifetime then reflects the fraction of the probe that is complexed with cations.

In a typical embodiment of the present invention, a doctor first decides which chemical or physical property is to be measured. Once this is decided, a probe capable of detecting the desired chemical/property is slid into a catheter or a catheter with an appropriate probe already embedded therein is used. The catheter can be a single or multilumen catheter design and/or extrusion. The doctor advances the catheter-based system to the desired location in the vasculature. Once the catheter-based system is in place, a data processing system is operated to send and receive signals. The received signals are processed by the data processing system to provide information on a display such that the doctor can view such information and determine how to proceed. The doctor can choose to perform a therapeutic procedure, such as angioplasty or stenting, or decide to do nothing. The doctor may decide that further information on that section of the vasculature is necessary and either continue with the same catheter-based probe or use a different catheter-based probe to try to obtain different chemical or physical data.

FIG. 1 illustrates generally one embodiment of a catheter based LBSFS system according to the present invention. A catheter 10 having a distal end 12 extends from a hub or handle 14. Distal end 12 of catheter 10 is insertable into a patient according to commonly known methods. Hub 14 accommodates a fiber optic bundle (not shown) which is connected to a light source 16 for imaging, a camera 18, a light source 20 for spectral analysis and an analyzer 22 for fluorescence spectrum analysis. Light source 16 and camera 18 are connected to the fiber optic bundle via a bifurcated imaging fiber 15a. Light source 20 and analyzer 22 are connected to the fiber optic bundle via a bifurcated imaging fiber 15b. A light source modulator 21 may also be connected to light source 20. Light sources 16 and 20 can be any continuous-wave signal or a high-repetition-rate pulsed laser. In one embodiment, light source 20 is a modulated light diode or high powered laser light source.

The light source is typically chosen based on the light wavelengths and light source power that facilitate the detection of the desired chemical analyte(s). Specifically, because fluorophores are sensitive to specific chemical analytes only in the presence of a particular wavelength or range of wavelengths (e.g. calcium imaging is possible in the wavelength range of 488–620 nm), the light source is typically chosen according to the which chemical analyte(s) is/are desired to be detected.

The light output could be filtered if desired, as a homogenized illumination improves the signal-to-noise ratio. If the red or near-IR spectral range is used, laser diodes could be used as the excitation source to further improve the signal-to-noise ratio. Camera 18 may be a CCD, CCCD or CMOS-based camera system or any similarly suitable camera system. A signal processing unit 24 is coupled to analyzer 22 for fluorescence spectrum analysis. Signal processing unit 24 typically processes a signal from visual or light source data to electronic data or vice versa.

Light source 16, camera 18, light source 20 and signal processing unit 24 are connected to a computer system 26, which is typically used for image acquisition, data processing and system control. Catheter 10 and hub 14 house a detection probe (not shown) that is coupled to the fiber optic bundle to which light source 16, camera 18, light source 20 and analyzer 20 are connected. It is appreciated that any or all of light source 16, camera 18, light source 20, analyzer 22, signal processing unit 24, and computer system 26 can be combined into an independent console unit. In one embodiment of the present invention, a probe assembly includes the detection probe, the fiber optic bundle, fibers 15a and 15b, light source 16, camera 18, light source 20, analyzer 22, signal processing unit 24, and computer system 26. In another embodiment of the present invention, a data processing system includes signal processing unit 24 and computer system 26.

It is appreciated that a variety of components can be used to help generate, transmit and receive fiber optic signals. For example, a monochromator can be used to receive light signals transmitted back from a tissue sample. The monochromator can also be fitted with a photodiode array detector, such as a 512 element intensified silicon photodiode array detector. Furthermore, a high resolution filter grating can be installed in the monochromator in order to sharpen the features displayed in the spectral response for easier peak recognition and spectral analysis. A pulse generator can be used to time the detector response from the output pulse of the laser light signal. An optical multichannel analyzer can be used to record the emission spectra. Dispersed spectra can be detected through the use of a photomultiplier tube, while Fourier transform infrared (FTIR) spectra can be obtained with a FTIR spectrometer. Additionally, scattered light can be collected into a spectrometer to capture any other potential chemical data.

Figure 2:
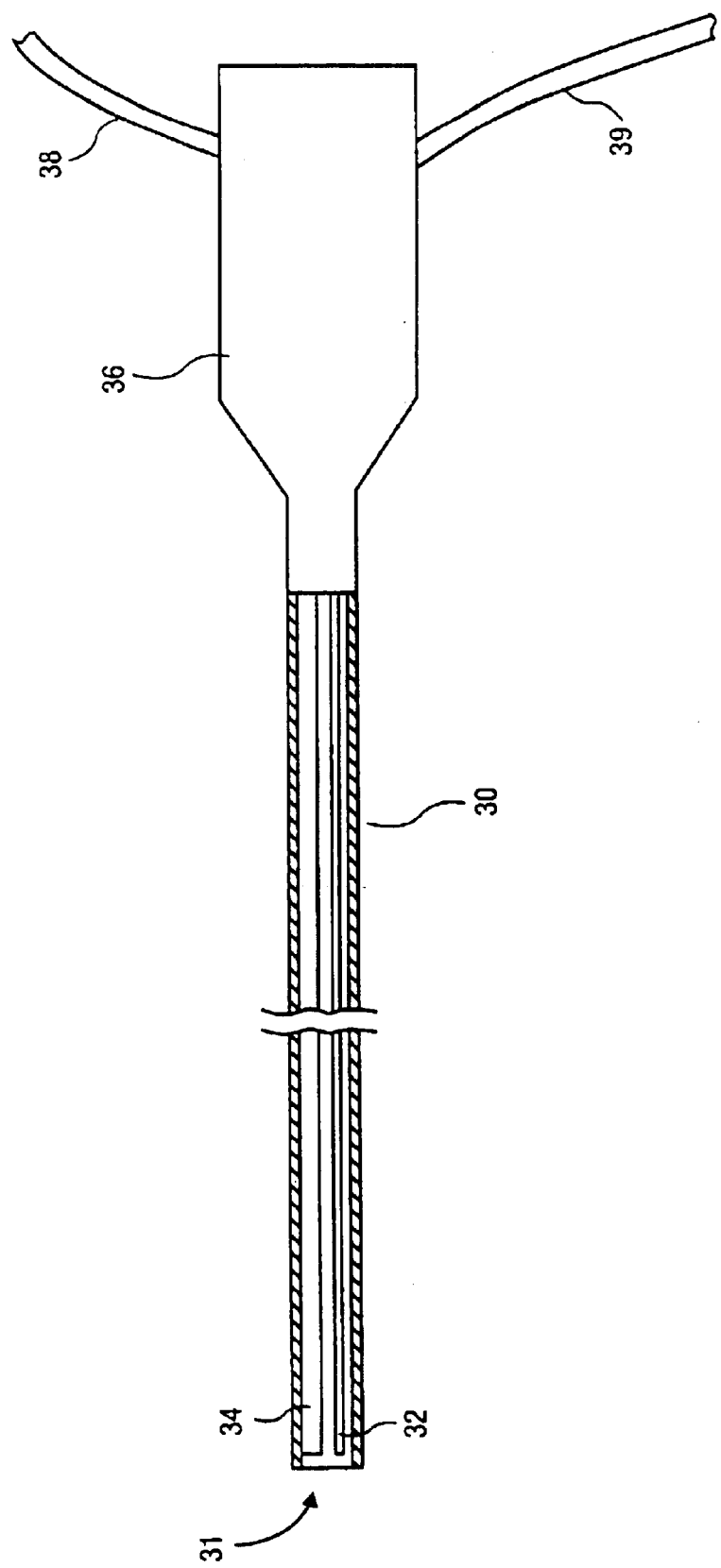
FIG. 2 shows a partial cutaway view of a catheter fitted with a detection probe in accordance with the teachings of the present invention.

FIG. 2 illustrates a partial cutaway view of a catheter 30 fitted with a detection probe 34. A light transmitting conduit 32 extends through catheter 30 toward a distal end 31 of catheter 30. Conduit 32 can be connected to any light source as described above. It should be noted that conduit 32 does not need to be separate from detection probe 34. For example, in one embodiment of the present invention, conduit 32 is housed within detection probe 34.

Catheter 30 is coupled to or integrally formed with a hub 36 which accommodates fiber optic conduits 38 and 39. Conduits 38 and 39 are connected to imaging and data processing components as previously described with respect to FIG. 1. In one embodiment, detection probe 34 is secured to the inner wall of catheter 30 such as with an epoxy or adhesive bonding material. In another embodiment, detection probe 34 is slideable within catheter 30 such that detection probe 34 can be advanced through catheter 30 toward distal end 31 and removed from catheter 30 via hub 36. Detection probe 34 is typically in the form of an elongated tube, although it is appreciated that other forms are possible.

In one embodiment of the present invention, conduit 32 and probe 34 are each connected individually to both conduits 38 and 39. Alternatively, a common fiber optic conduit or bundle housed within hub 36 can be used to connect conduit 32, probe 34 and conduits 38 and 39.

Figure 3A:
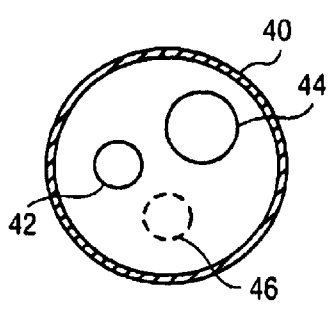
FIG. 3A shows a front view of an embodiment of a catheter fitted with a detection probe in accordance with the teachings of the present invention.
Figure 3B:
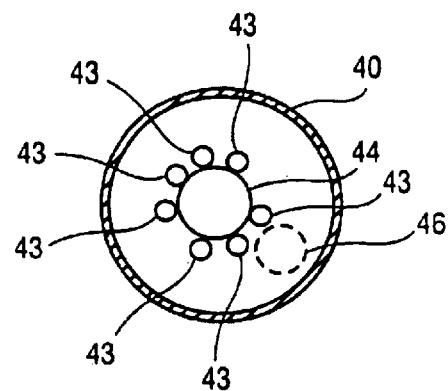
FIG. 3B shows a front view of another embodiment of a catheter fitted with a detection probe in accordance with the teachings of the present invention

FIGS. 3A and 3B show front views of two embodiments of a catheter 40 fitted with a detection probe 44. In FIG. 3A, detection probe 44 is disposed freely within catheter 40 such that detection probe 44 is slideable within catheter 40. A fiber optic conduit 42, such as for a light source, is also disposed freely within catheter 40. The lumen of catheter 40 may also be large enough to accommodate a guidewire 46 (optional). In FIG. 3B, detection probe 44 is disposed freely within catheter 40 and is surrounded by fiber optic conduits 43 which may be coupled to different light sources. In both FIGS. 3A and 3B, catheter 40 may also accommodate a lumen for the flushing of fluid (e.g. saline, heparin).

FIGS. 4A and 4B show two embodiments of a catheter 60 fitted with a detection probe which are positioned adjacent to a diseased area of a vessel 50. A lesion having areas 51a and 51b lines the inner wall of vessel 50, leaving a narrow passageway 53 between lesion areas 51a and 51b.

In FIG. 4A, catheter 60 houses a detection probe 54a and a light transmitting conduit 52. It should be noted that conduit 52 can be housed within probe 54a or attached to probe 54a, or probe 54a can be housed within conduit 52. Probe 54a is shown unattached to the inner wall of catheter 60 such that probe 54a is slideable through catheter 60. In one embodiment of the present invention, catheter 60 is first advanced through vessel 50 to the diseased area having lesions 51a and 51b. Probe 54a is then advanced through catheter 60 toward the diseased area such that the desired chemical and/or physical information can be obtained. If probe 54a is fixed to the inner wall of catheter 60, then probe 54a will be moved to the target area as catheter 60 is moved to the target area.

In FIG. 4B, catheter 60 houses a detection probe 54b having a probe end 55 which faces the inner wall of catheter 60. Probe 54b can house one or more light transmitting conduits (not shown). Probe 54b is slideable through catheter 60 and rotatable such that probe end 55 can be oriented in a variety of positions. In one embodiment of the present invention, catheter 60 is first advanced through vessel 50 to the diseased area having lesions 51a and 51b such that part of catheter 60 is located within passageway 53. Probe 54b is then advanced through catheter 60 to the diseased area such that probe end 55 can be positioned along the lesion and rotated to obtain different radial views; thus, the desired chemical and/or physical information can be obtained.

Figure 5A:
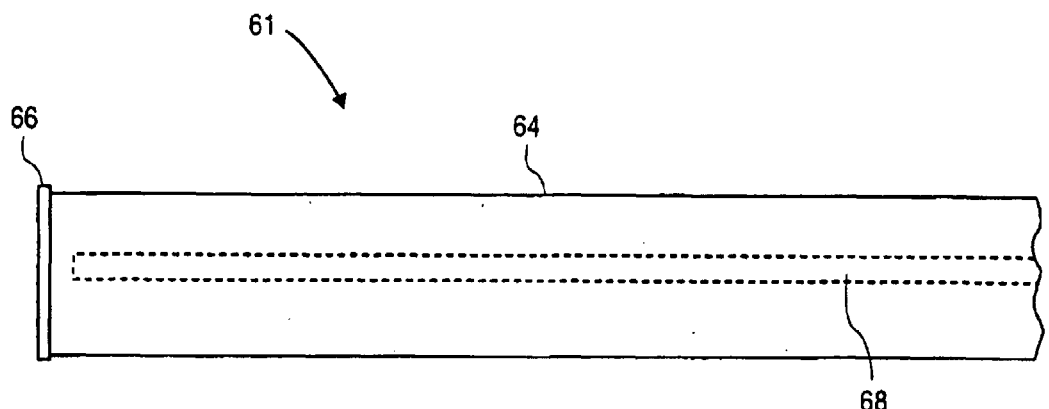
FIG. 5A shows a side view of one embodiment of a detection probe in accordance with the teachings of the present invention.
Figure 5B:
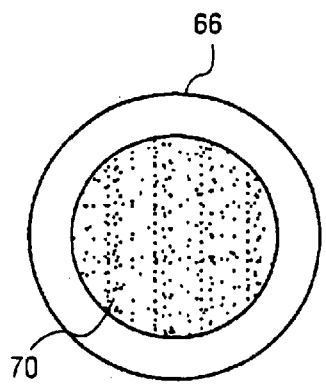
FIG. 5B shows a front view of the detection probe shown in FIG. 5A.
Figure 5C:
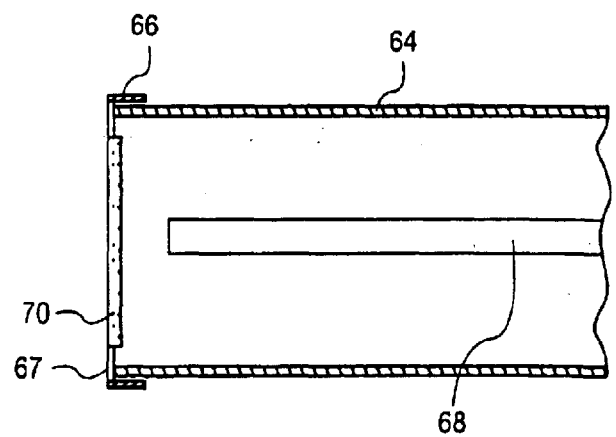
FIG. 5C shows a cutaway view of the detection probe shown in FIG. 5A.

FIGS. 5A–5C show side, front and cutaway views, respectively, of one embodiment of a detection probe 61 according to the present invention. Probe 61 is formed with a main housing 64 having an end capped by an optically clear cover 66. Cover 66 may be either force fitted onto housing 64 or bonded to housing 64 using any suitable adhesive or bonding material. Housing 64 is typically in the shape of an elongated tube, but it is appreciated that other configurations may be used as long as probe 61 is either slideable within a catheter or bondable to the inner wall of a catheter.

In one embodiment of the present invention, a fiber optic bundle 68 is housed freely within housing 64 such that bundle 68 and housing 64 can be moved relative to each other. Alternatively, bundle 68 can be coupled to cover 66 or housing 64 such that bundle 68 moves with housing 64. Bundle 68 can be a single fiber optic conduit for receiving optical information which is transmitted back to an external analyzer. In such an embodiment, a fiber optic conduit external to housing 64 but typically located within the catheter is used to transmit light from an external light source. In another embodiment, bundle 68 has two fiber optic conduits, one of which transmits light from an external light source and the other of which receives optical information. It should be noted that multiple fiber optic conduits may also be used.

A membrane 70 embedded with a fluorophore is attached to the inner face 67 of cover 66. The attachment can be performed via a press fit, a snap fit, an adhesive, a dip coating, or other suitable techniques. Typically, a fluorophore is adsorbed into membrane 70, which can be, for example, a filler free silicone. Alternatively, a fluorophore may be adsorbed into a silica gel before being embedded into membrane 70. If cover 66 is removable from housing 64, then different fluorophores can be used in detection probe 61 without using different main housings. For example, when a different chemical analyte is desired to be detected, probe 61 can be removed from the catheter and cover 66 can be replaced with a cover formed with an appropriate fluorophore. Probe 61 can then be reinserted into the catheter and advanced to the target area of the vasculature.

Figure 6:
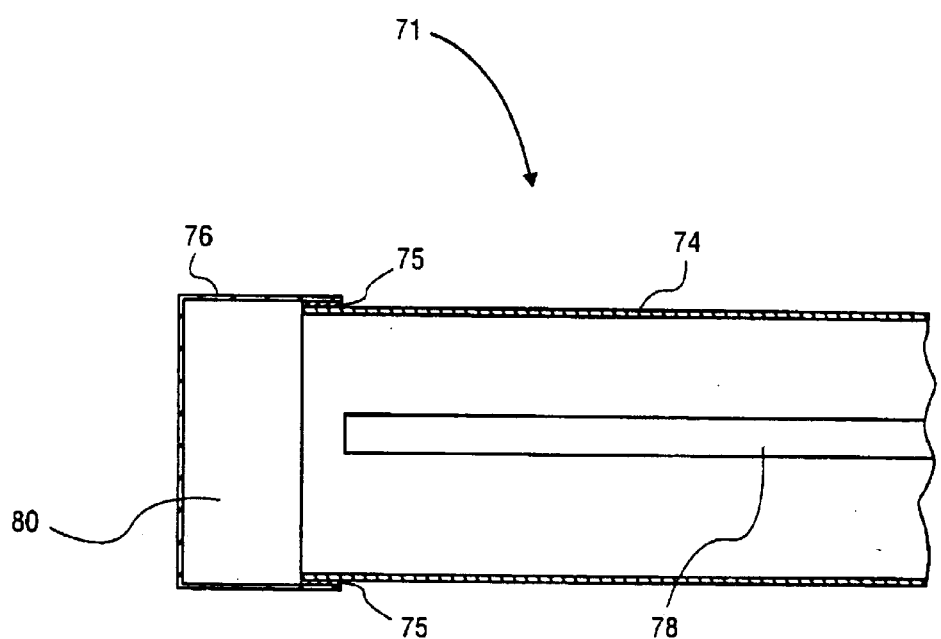
FIG. 6 shows a cutaway view of another embodiment of a detection probe in accordance with the teachings of the present invention.

FIG. 6 illustrates a cutaway view of another embodiment of a detection probe 71 according to the present invention. Probe 71 is formed with a main housing 74 having an end capped by a cap 76. Housing 74 is typically in the shape of an elongated tube, but it is appreciated that other configurations may be used as long as probe 71 is either slideable within a catheter or bondable to the inner wall of a catheter. A fiber optic or fiber optic bundle 78, similar to bundle 68 described above, is housed freely within housing 74. Cap 76 is bonded to housing 74 by an epoxy bond 75 or other suitable connection. When cap 76 is bonded to housing 74, a reservoir 80 is formed at an end of housing 74 to hold a fluid (e.g. purified, sterile water) which carries a sensing indicator (e.g. a fluorophore). The fluid typically resides primarily within reservoir 80, although it is appreciated that the fluid can also flow through housing 74. Bond 75 prevents the fluid from leaking out of reservoir 80. Cap 76 includes a membrane if the sensing indicator detects a chemical analyte through a bond or a chemical interaction. Cap 76 is made of an optically clear glass or polymer cover if the sensing indicator is of the type which detects a chemical analyte through changes in the wavelength and frequency of the light being emitted. It is appreciated that reservoir 80 may be formed on the side of housing 74 rather than at the end of housing 74. It is also appreciated that multiple reservoirs may be formed in a variety of configurations (e.g. in series or in parallel) such that each reservoir holds a different sensing indicator.

An example of a diagnostic procedure according to the present invention will now be described generally. A guidewire is placed at or through a lesion. A sensing catheter having a fluorophore-embedded probe disposed therethrough is then advanced to the lesion. A light source directed to the vicinity of the fluorophore is turned on at a wavelength that facilitates the chosen fluorophore's sensitivity to a chemical analyte that is desired to be detected. The resulting signal received from the probe containing information about the lesion area is processed by signal processing components, such as those described in conjunction with FIG. 1. A readout from the signal processing unit, computer monitor, or other output device connected to the signal processing components indicates if the chemical analyte is present, and if so, in what quantity. At this point, a determination can be made as to what type of intervention (e.g. stenting, angioplasty, atherectomy, etc.) is more appropriate to treat the encountered vascular condition. If the probe is removable, as described previously according to one embodiment of the present invention, then the catheter and probe can be withdrawn such that a different probe can be substituted to detect a different chemical analyte.

Because the detection probe is slideable according to one embodiment of the present invention, it is interchangeable with a variety of catheters, such as imaging catheters, diagnostic catheters and alternative treatment catheters. For example, the detection probe can be positioned at different points within a single or dual balloon angioplasty catheter.

The present invention can also give doctors the capability of detecting a variety of chemicals, chemical interactions and physical properties at a target area in a patient's vasculature. For example, the present invention could be used first to perform an assessment at the site of a lesion, and it could be used later to measure changes that occur after or during a treatment such as angioplasty or stenting. Doctors could then be more informed and potentially provide more appropriate treatment to their patients. Additionally, the present invention could be used in conjunction with photo-angioplasty (e.g. photoablation or ablative photodecomposition) or photodynamic therapy. In such treatments, a therapeutic chemical is supplied to a region, such as a lesion, and combined with a compound that supports the activation or release of the therapeutic agent to the tissue sample. An example of such a compound is a texaphyrin, which is a porphyrin that is derived from hemoglobin and known for its light sensitivity.

Although the present invention has been described specifically in relation to the detecting of chemical analytes, it is appreciated that other molecules, such as cancer cells and vascular cell adhesion molecules, may be targeted for detection using appropriate fluorophores or chemosphores.

Using the present invention in conjunction with the diagnosis and treatment of cancer can improve cancer treatment strategies and provide more precise targeting of tumors, which facilitates the selection of an appropriate course of treatment. If a fluorochrome is used to target protease activity, and an appropriate light source wavelength is also used, then the detection and proper diagnosis of a tumor is possible. For example, a 673 nm wavelength light is one appropriate possibility. The fluorochrome can be delivered locally at the site of the tumor or systemically. Because tumorous tissue tends to have a high level of protease activity, it fluoresces in the presence of light having certain wavelengths. A graft copolymer of poly-L-lysine protected by side chains of methoxypolyethylene glycol (MPEG) can be synthesized and used to deliver the fluorochromes to the tumor. A fluorochrome such as Cy 5.5 can be attached to the backbone of the copolymer.

The present invention can also be used to track blood flow through the use of markers for either red blood cells (RBCs) or white blood cells (WBCs). In addition, the presence of RBCs and WBCs can be detected. The presence of RBCs could indicate a rupture, tear, dissection or break, and the presence of WBCs could indicate potential infection. Fluorescent nucleic acids, such as SYTO 16 (green) and SYTO 59 (red), can be used to detect the presence and flow WBCs. Such nucleic acids can permeate the cell membrane, be absorbed efficiently and provide a distinct fluorescence signal. Indocarbocyanine D-307 (red) can be used to detect the presence and flow of RBCs.

SYTO 16 can be excited with a 488 nm wavelength light, and the cells absorbed with SYTO 16 would fluoresce at 518 nm. If a 633 nm wavelength light is used for SYTO 59 and D-307, they would have an absorbance and emittance of 630 nm and 650 nm, respectively, for the former, and 644 nm and 665 nm, respectively, for the latter.

Particular applications of the just described blood flow tracking include the detection of blood flow at: the site of a chronic total occlusion; the site of a stent placed at a bifurcation; the esophagus; the stomach; the colon; the uterus; saphenous vein grafts; heart valves; and other body cavities and lumens.

The present invention can also be used to facilitate the diagnosis and treatment of strokes, neurodegenerative disorders, Huntington's Disease, and epilepsy. Using a glutamate sensor in conjunction with the catheter based LBSFS system of the present invention could provide detection of strokes and other conditions that are difficult to detect in advance. Such a glutamate sensing system would typically include glutamate dehydrogenase embedded at an end of a catheter based probe. Glutamate is an amino acid, and its presence and level of concentration may be an indication as to the presence and severity of a stroke. As a neurotransmitter, glutamate is also implicated in the destruction of neurons in the brain, especially when it is detected in high concentrations.

In the foregoing detailed description, the apparatus and method of the present invention have been described with reference to specific exemplary embodiments. However, it will be evident that various modifications and changes may be made without departing from the broader scope and spirit of the present invention. The present specification and figures are accordingly to be regarded as illustrative rather than restrictive.

What is claimed is:

1. A medical diagnostic apparatus comprising:
   a catheter having a first end and a second end and a lumen;
   a detection probe insertable in said catheter near said first end and slidable through said lumen toward said second end, said detection probe capable of detecting a chemical analyte; and
   a data processing system coupled to said detection probe, wherein the detection probe further comprises:
      a main housing having a optically clear cover positioned along the length thereof;
      a fiber optic bundle housed freely within the housing; and
      a membrane embedded with a fluorophore and attached to an inner surface of the optically clear cover.

2. The apparatus of claim 1, wherein the detection probe may be removed from the catheter, the optically clear cover replaced, and the probe inserted into the same or a different catheter.

3. A medical diagnostic apparatus comprising:
   a catheter having a first end and a second end and a lumen;
   a detection probe insertable in said catheter near said first end and slidable through said lumen toward said second end, said detection probe capable of detecting a chemical analyte; and
   a data processing system coupled to said detection probe, wherein the detection probe is for use with glutamate or glutamate dehydrogenase to diagnose one of a stroke, a neurodegenerative disorder, Huntington's Disease, or epilepsy.

4. A medical diagnostic apparatus comprising:
   a catheter having a first end and a second end and a lumen;
   a detection probe insertable in said catheter near said first end and slidable through said lumen toward said second end, said detection probe capable of detecting a chemical analyte; and
   a data processing system coupled to said detection probe, wherein the detection probe is to diagnose one of a cancer cell and a vascular cell adhesion molecule.

5. A medical diagnostic apparatus comprising:
   a catheter having a first end and a second end and a lumen;
   a detection probe insertable in said catheter near said first end and slidable through said lumen toward said second end, said detection probe capable of detecting a chemical analyte; and
   a data processing system coupled to said detection probe, wherein the detection probe includes a fluorescent nucleic acid to detect a presence at least one of white blood cells and red blood cells.

\* \* \* \* \*